United States Patent [19]

Soeda et al.

[11] Patent Number: 5,518,742
[45] Date of Patent: May 21, 1996

[54] ENZYME PREPARATION FOR PRODUCING BOUND-FORMED FOOD

[75] Inventors: Takahiko Soeda; Katsutoshi Yamazaki; Shoji Sakaguchi; Chiho Ishii; Keiko Hondou, all of Kawasaki, Japan

[73] Assignee: Ajinomoto Co., Inc., Tokyo, Japan

[21] Appl. No.: 443,388

[22] Filed: May 17, 1995

Related U.S. Application Data

[63] Continuation of Ser. No. 69,119, May 28, 1993, abandoned.

[30] Foreign Application Priority Data

Jun. 2, 1992 [JP] Japan ..................... 4-141693
Feb. 5, 1993 [JP] Japan ..................... 5-018541

[51] Int. Cl.⁶ .................. A23L 1/317; A23J 3/04; A23J 3/10; A23J 3/34
[52] U.S. Cl. .................. 426/63; 426/574; 426/652; 426/802; 426/59
[58] Field of Search .................. 426/7, 42, 56, 426/59, 63, 574, 652, 802

[56] References Cited

U.S. PATENT DOCUMENTS 4,917,904  4/1990  Wakamed et al. .................. 426/7

FOREIGN PATENT DOCUMENTS 2086748  9/1988  Japan.
2135071  11/1988  Japan.
2079956  1/1989  Japan.
3232478  2/1990  Japan.
4079842  3/1992  Japan.
4207194  7/1992  Japan.

OTHER PUBLICATIONS

European Search Report dated Jul. 13, 1994.
"Crosslinking of myosin and casein by the enzyme transglutaminase"; L. Kurth; *Food Technology in Australia;* vol. 35(9), Sep., 1983.

*Primary Examiner*—Donald E. Czaja
*Assistant Examiner*—Curtis E. Sherrer
*Attorney, Agent, or Firm*—Oblon, Spivak, McClelland, Maier & Neustadt

[57] ABSTRACT

An enzyme preparation for bound-formed food use which comprises transglutaminase, a casein and an edible surface active agent. The enzyme preparation strongly binds raw food materials, and the resulting bound-formed foods have an excellent taste and savor.

6 Claims, No Drawings

ENZYME PREPARATION FOR PRODUCING BOUND-FORMED FOOD

This application is a Continuation of application Ser. No. 08/069,119, filed on May 28, 1993, now abandoned.

BACKGROUND OF THE INVENTION

1. Technical Field

This invention relates to an enzyme preparation for use in the production of bound-formed food (i.e., three-dimensionally-formed food by binding), and to a process for the production of bound-formed food.

2. Prior Art

Various processes have been attempted in relation to the binding forming of food raw materials. The following illustrates six typical binding forming processes, with problems involved in each process.

For example, (1) Japanese Patent Application Laying-Open (Kokai) No. Sho 55-13031 discloses a process in which binding of small pieces of animal meat, fish meat and the like is effected by the use of konjak powder, (2) Japanese Patent Application Laying-Open (Kokai) No. Sho 53-20457 discloses a process in which binding of food proteins such as milk protein, egg protein, wheat protein, soybean protein and the like is effected by the use of enzyme hydrolyzates of these proteins and kitchen salt, and (3) Japanese Patent Application Laying-Open (Kokai) No. Sho 53-26345 discloses a process in which binding of meat pieces is effected by applying dried powder of a raw fish meat paste to the meat pieces and then heating the thus treated pieces.

However, meat pieces and food proteins bound by such processes are apt to be broken, e.g., when they are made into block meat or sliced meat in the raw state, thus causing a problem in that sufficiently bound conditions cannot be maintained till their cooking or further processing.

Also included are (4) a process in which binding of meat pieces is effected by applying an alginate to the meat pieces and then gelatinizing it by the addition of a calcium salt, and (5) a process disclosed in Japanese Patent Application Laying-Open (Kokai) No. Hei 2-268665 in which binding of meat pieces is effected by the combined use of a heat-coagulating protein such as wheat protein or the like and an alkaline earth metal agent such as calcium oxide, calcium hydroxide or the like which gives alkalinity when dissolved in water.

However, in the former case (aforementioned process (4)), the process not only shows low binding effect but also has inferior workability because it requires two addition steps, namely application of an alginate to the meat pieces and subsequent addition of calcium salt or the like. In addition to this, it has another disadvantage in that the resulting product shows poor appearance due to the partly remaining insoluble calcium. In the latter case (process (5)), on the other hand, not only the process shows poor binding effect but also the resulting product is not desirable from the view point of the taste inherent in meat because of its bitter aftertaste, proteinous odor and the like.

In addition, (6) Japanese Patent Application Laying-Open (Kokai) No. Hei 2-79956 discloses a process in which binding of meat pieces is effected by making the meat piece surface viscous to secure a high binding effect, that is, by adding kitchen salt to the meat pieces and then crumpling them with hands or mechanically using a tumbler to liquate myosin.

However, this process also has disadvantages in that it requires a large quantity of kitchen salt which causes a salty aftertaste and it also requires heating to effect the binding, thus resulting in the considerably limited use of the bound meat pieces for food products.

(Problems to be Solved by the Invention)

Because of such problems involved in the prior art, great concern has been directed, in the field of process food industries, toward the development of a binding agent and a binding method by which the production of bound-formed foods (i.e., three-dimensionally-formed foods by binding) can be achieved with such effects that (1) joint use of kitchen salt is not necessary and a liquation step of protein such as myosin to increase viscosity is not required, (2) meat pieces and food materials can be bound strongly in their unheated raw state, and (3) bound-formed foods as the final products have no problems in terms of their taste and savor.

In addition, since the aforementioned process disclosed in Japanese Patent Application Laying-Open (Kokai) No. Hei 2-79956 is limited in its application to animal meat only, great concern has also been directed, in the field of process food industries, toward the establishment of a binding agent and a binding method having a wide range of applicability so that they can be applied not only to animal meat but also to other various food raw materials especially fish slices, fishes and shellfishes such as squids, cuttlefishes, crabs and the like, and fish eggs such as salmon roe, herring roe, salted salmon roe, salted pollack roe and the like.

Establishment of these techniques has a great social significance from the viewpoint of the effective utilization of natural resources.

SUMMARY OF THE INVENTION

In an aspect of the present invention, there is provided an enzyme preparation for use in the binding of food raw materials comprising transglutaminase and a casein-containing material as active ingredients.

In another aspect of the present invention, there is provided an enzyme preparation for the same use comprising an edible surface active agent as wel as the two above-mentioned active ingredients.

In a third aspect of the present invention, there is provided a process for production of bound-formed foods comprising an enzyme preparation of the first or second aspect of the present invention to a raw food material and allowing said enzyme preparation to exert its function.

And, in a fourth aspect of the present invention, there is provided a process for the same purpose comprising adding transglutaminase and a casein or transglutaminase, a casein and an edible surface active agent to a raw food material, and allowing them to exert their fuctions.

DETAILED DESCRIPTION OF THE INVENTION

With the aim of coming up to the expectations described in the foregoing, the inventors of the present invention have conducted intensive studies and found that a combination of casein and transglutaminase can exert excellent binding effect on the aforementioned food materials and that such an binding effect can be further improved by the use of a surface active agent. The present invention has been accomplished on the basis of these findings.

The present invention will be described below in detail.

A first embodiment of the present invention relates to an enzyme preparation for use in the binding of food raw materials, which comprises transglutaminase and a casein as active ingredients.

This enzyme preparation contains transglutaminase and a casein as essential active ingredients.

As is universally known, transglutaminase is an enzyme so-called "amine introducing system" which catalyzes introduction of primary amines, ammonia, hydroxylamine, diamino acids, monoamino acids, esters and the like into receptor proteins and peptides such as casein, β-lactoglobulin, insulin and the like. In a system in which a protein to be used in the present invention is contained, it is known that this enzyme catalyzes a crosslink formation reaction in which the ε-amino groups of the lysine residues in the protein replace the glutamine amino groups (cf. Japanese Patent Publication (Kokoku) No. Hei 1-50382 and Japanese Patent Application Laying-Open (Kokai) No. Hei 1- 27471, corresponding to U.S. Pat. No. 5156956).

It is known that transglutaminase is found with high activity in the liver of mammals such as guinea pigs and the like, as well as in several types of microorganisms, plants and fishes.

Transglutaminase to be used in the present invention is not particularly limited in its origin. That is, its origin is not restricted provided that the enzyme has a transglutaminase activity. Examples of useful transglutaminase include those originating from the guinea pig liver (Japanese Patent Publication (Kokoku) No. Hei 1-50382), from plants, from fishes (for example, those reported by N. Seki et al. in Abstract of Papers, 1988 Autumn Meeting of the Japanese Society of Scientific Fisheries, page 167, and in Abstract of Papers, 1990 Spring Meeting of the Japanese Society of Scientific Fisheries, page 219), and from microorganisms (Japanese Patent Application Laying-Open (Kokai) No. Hei 1-27471, op. cit.), as well as those prepared by means of recombinant DNA techniques (Japanese Patent Application Laying-Open (Kokai) No. Hei 1-300889).

Transglutaminase can be classified into calcium-independent and calcium-dependent types. Examples of the former type include the aforementioned ones of microbial origin. Examples of the latter type include the aforementioned ones of guinea pig liver origin and of fish origin. Though both types of transglutaminase can be used, the calcium-independent type is preferable from the viewpoint of application to a wide range of foods.

Transglutaminase originating from a microorganism belonging to the genus Streptoverticillium is particularly preferred, because it is calcium-independent and can be obtained easily at a low cost (Japanese Patent Application Laying-Open (Kokai) No. Hei 1-27471, op. cit.).

Though not particularly limited, an enzyme preparation of the present invention may generally contain transglutaminase in an amount of from 1 to 50,000 units, preferably from 10 to 5,000 units, per 1 g of protein in the enzyme preparation containing casein and the like, from the viewpoint of workability in using it.

As a matter of course, it is preferable to use highly purified transglutaminase in the present invention.

Caseins as the other active ingredient of the enzyme preparation of the present invention may be not only a so-called casein but also in the form of a salt such as sodium caseinate, calcium caseinate, potassium caseinate or the like, in the form of casein-containing milk powder or in the digested form obtained by hydrolyzing any of these casein sources with enzyme, acid or alkali. Though the casein can be used in any of these forms in the present invention, it may be preferable to use sodium caseinate from the viewpoint of binding capacity, workability, economy, availability, good water solubility and the like. As a matter of course, two or more casein sources selected from casein, sodium caseinate, calcium caseinate, potassium caseinate, milk powder and the like may be used in combination.

The enzyme preparation of the present invention may generally contain a casein in an amount of from 20 to 99 weight parts, preferably from 70 to 90 weight parts, in 100 weight parts of the enzyme preparation, from the viewpoint of its good performance.

In general, caseins such as caseinate, sodium caseinate and the like are used as a modifier in emulsibility for process foods. However, virtually nothing is known about the combined use of a casein with transglutaminase as a binding agent of proteinous food raw materials. As will be described in the following, such a combination causes markedly excellent effects.

It is generally known that, when a bound beef is prepared, binding of meat pieces to one another cannot be effected without the use of a binding agent. The inventors of the present invention have prepared prototype bound beef samples A, B and C by mixing such meat pieces with (A) 1% sodium caseinate only, (B) only transglutaminase in an amount of 1 unit per 1 g meat or (C) 1% sodium caseinate and transglutaminase in an amount of 1 unit per 1 g meat and then allowing each of the resulting mixtures to stand still at ordinary temperature for 30 minutes. Tensile strength ($g/cm^2$) of each of the thus prepared prototype samples was measured using a rheometer manufactured by Fudo Kogyo Co., Ltd.

Tensile strengths ($g/cm^2$) of the three prototype samples were found to be A=25, B=41 and C=185, thus showing a pronounced synergistic effect caused by the combined use of transglutaminase and a casein. In general, binding of raw materials or cooking and processing performance of the bound product cannot be regarded as effective or acceptable when the tensile strength is less than 100 $g/cm^2$.

It is evident from this that such an excellent binding capacity is expressed for the first time when transglutaminase and casein are used in combination. The binding capacity expressed by such a synergistic effect can fit for the handling of the bound meat when processed, without causing separation of meat pieces from one another in the raw state.

Incidentally, 2 to 3 commercially available binding agents were used according to the respective prescriptions and the resulting bound products were evaluated in the same manner as described above. The tensile strengths were within a range of from 30 to 70 $g/cm^2$, with no values exceeding 100 $g/cm^2$. These results also support marked excellence in the techniques according to the present invention.

The enzyme preparation of the present invention may further contain various optional ingredients, in addition to the essential active ingredients transglutaminase and caseins.

One of such optional ingredients is a food filler. Any of common food fillers can be used without particular limitation, which include for example lactose, sucrose, maltitol, mannitol, sorbitol, dextrin, branched dextrin, cyclodextrin, glucose, starches such as potato starch, polysaccharides, gums, emulsifiers, pectin, oils and fats and the like. Of these, starches such as potato starch and branched dextrin are particularly preferred because they do not exert influence on the binding effect of raw food materials by transglutaminase and casein and they have no taste or odor. These food fillers may be used singly or as a mixture of two or more. Such food fillers are useful for giving characteristic properties to foods, especially those properties required in addition to the binding capacity, such as a juicy feeling, a good throat-passing feeling and a soft eating touch even when the food is cooled.

In addition to these food fillers such as branched dextrin and the like, the enzyme preparation of the present invention may also contain proteins other than caseins, as other optional component, which include soybean proteins such as isolated soybean protein, concentrated soybean protein, extracted soybean protein, defatted soybean protein and the like; wheat proteins such as wheat gluten and the like and wheat flour which contains wheat proteins; corn protein; and egg proteins such as albumen, egg albumin and the like. These proteins also impart a binding function.

Still other optional components may be used appropriately as will be explained below.

The enzyme preparation of the present invention is used for example by directly applying it to a raw food material to be treated or by dissolving or suspending it in water and then mixing the resultant solution or suspension with the raw material. Especially, if the enzyme preparation is used by dissolving or suspending it in water and then mixing the resulting solution or suspension with a raw food material, partial inactivation of the transglutaminase may occur due to its denaturation when the pH value of the solution or suspension is outside the stable pH range of transglutaminase or when the ionic strength of the solution or suspension is outside the stable ionic strength range of the enzyme.

As for the former case, denaturation of transglutaminase can be prevented by incorporating into the enzyme preparation of the present invention a pH adjusting agent such as sodium hydrogencarbonate, sodium citrate, sodium phosphate or the like in such an amount that the final pH of the enzyme preparation when dissolved or suspended in water is adjusted to within the stable pH range of transglutaminase. As for the latter case, denaturation of transglutaminase can be prevented by incorporating into the enzyme preparation of the present invention an electrolyte such as sodium chloride, potassium chloride or the like in such an amount that the final ionic strength of the enzyme preparation when dissolved or suspended in water is adjusted to within the stable ionic strength range of transglutaminase. It is especially preferable to incorporating an electrolyte such as sodium chloride, potassium chloride or the like in advance into the enzyme preparation from the viewpoint of preventing denaturation of transglutaminase.

If desired, the enzyme preparation of the present invention may further contain appropriately seasonings, sugar, coloring agents, color fixing agents, ascorbic acid or salts thereof, emulsifiers, oils and fats and the like, as well as enzyme stabilizers such as calcium chloride, sodium sulfite, sodium bicarbonate and the like (Japanese Patent Application Laying-Open (Kokai) No. Hei 4-207194).

The enzyme preparation of the present invention can be obtained in a usual way by uniformly mixing transglutaminase and casein both as the main components and if desired, further components such as food fillers, electrolytes and the like.

The enzyme preparation may be in any optional forms with no particular limitation, such as powders, granules, solutions, capsules and the like.

Finally, bound-formed foods produced with the use of the inventive enzyme preparation and their raw materials will be described in the following.

As these raw materials, there can be mentioned, for example, proteinous raw food materials such as animal meats such as beef, pork, horse meat, sheep meat, goat meat, rabbit meat, chicken and the like; and fishes and shellfishes including not only biologically classified fishes such as Osteichthyes, Chondrichthyes and the like but also crustaceans, molluscs, shellfishes and the like, such as bony fishes including Alaska pollack, saury pike, horse mackerel, sardine, skipjack, salmon, sharp-toothed eel, sea bream, tongue sole, flatfish and the like, cartilaginous fishes including shark, ray and the like, crustaceans including prawns, shrimps, crabs, lobsters and the like, molluscs including squid, cuttlefish, octopus and the like, and shellfishes including scallop, abalone and the like, and fish eggs such as salmon roe, salted salmon roe and the like, these examples being primary raw food materials, as well as animal meat or fish jelly products such as ham, hamburg steak, sausage, Japanese kamaboko, Japanese chikuwa, Japanese hampen, Japanese tsumire and the like which are processed and produced from their raw materials such as animal meat, Alaska pollack, squid, cuttlefish, sardine and the like, and process foods such as cheeses, Japanese tofu, noodles, dried laver and the like, these examples being secondary raw food materials.

An example of the proteinous process food which can be as such used as a raw material for the bound-formed food of the present invention will be described later in Example 29 in which cheese and ham, both being process foods, were used as raw materials.

Although sliced cucumber was used as one of the raw materials in the same Example, cucumber, carrot, cabbage, Japanese konjak and the like can be singly or taken together as the raw material of the bound-formed food of the present invention. Vegetables and fruits are, however, used very often together with proteinous raw materials, which results in their value added.

Furthermore, any solid foods such as bean, biscuit, cracker, caramel, chocolate, cake, rice snack, potato chip, cookie, pie, candy and the like can be raw food material for the production of bound-formed foods of the present invention.

The bound-formed foods produced from these raw materials include not only bound products of chicken, animal meat, fish meat and the like, which can be made into steak, and ham, sausage, hamburg steak, meat balls, Japanese kamaboko, Japanese chikuwa, Japanese hampen and the like, but also other bound-formed foods which are not known in the prior art, such as a product having a novel structure as will be described later in Example 32.

A second embodiment of the present invention relates to an enzyme preparation for use in the binding of food raw materials, which comprises transglutaminase, a casein and an edible (or physiologically acceptable) surface active agent (surfactant) as active ingredients.

The enzyme preparation according to the second embodiment of the present invention is different from the enzyme preparation of the aforementioned first embodiment of the present invention in terms of the essential active ingredients, because the second embodiment preparation further contains an edible surface active agent as the additional essential active ingredient.

As has been described in the foregoing, the enzyme preparation of the first embodiment of the present invention is an epoch-making industrially producible food binding agent, because it has a markedly strong binding effect on raw food materials due to the joint use of transglutaminase and a casein and is free from any taste or odor, but with some points to be further improved as will be described in the following.

That is, in order to obtain sufficient binding effect with a small amount of this enzyme preparation, it is necessary for it to be mixed with raw food materials easily and uniformly. In this instance, the enzyme preparation is directly applied to the raw food material to be treated or added to the raw material after dispersed or dissolved in water or the like.

When these two ways are compared, the latter in which the enzyme preparation is added to the raw material after dispersed or dissolved in water or the like is preferable judging from the binding effect. However, since transglutaminase starts its reaction with caseins immediately after dispersion or dissolution of the enzyme preparation, it is necessary to disperse or dissolve the enzyme preparation within a short period of time and mix the suspension or solution quickly with the raw food material to be treated.

However, this enzyme preparation causes a problem when it is dispersed or dissolved in water, because a casein is apt to form loose lumps which are difficult to be dispersed or dissolved uniformly. Though the thus formed loose lumps could be disrupted and dispersed or dissolved by force by means of high speed agitation and the like, rapid changes in the surface tension caused by the high speed agitation might entail inactivation of transglutaminase and, as the result, reduction of the binding effect on raw food materials.

Accordingly, the inventors of the present invention have conducted intensive studies with the aim of overcoming such problems. As a result, it has been found that the enzyme preparation of the first embodiment of the present invention can be dispersed or dissolved in water quickly and easily without spoiling its inherent effect to bind raw food materials, when an edible surface active agent is added to transglutaminase and a casein. The enzyme preparation of the second embodiment of the present invention has been developed on the basis of this finding.

The edible surface active agent to be used as a third essential active ingredient of this enzyme preparation is not particularly limited, provided that it is acceptable as a food additive, with typical examples including monoglycerides and derivatives thereof, sucrose fatty acid esters, sorbitan fatty acid esters, propylene glycol fatty acid esters, polyglycerol esters, "polysorbate" and the like. Of these, sucrose fatty acid esters, polyglycerol esters and "polysorbate" having an HLB value of 8 or more are particularly preferred in view of their high water dispersion improving effect, high water solubility and tasteless and odorless nature.

These edible surface active agents may be incorporated singly or as a mixture of two or more in this enzyme preparation.

The enzyme preparation contains the edible surface active agent in such an amount that the effect resultant from its blending can be expressed, namely in an amount generally from 0.01 to 15 weight % based on the total amount of the preparation.

As described in the foregoing, this enzyme preparation is different from the enzyme preparation of the first embodiment of the present invention only in terms of the use of an eidible surface active agent. In other words, other optional components to be included, process per se for the production of this enzyme preparation, dosage forms and the like can be the same as those described in the foregoing, and therefore no further explanation will be required herein.

As has been described, caseins such as casein, sodium caseinate and the like are generally used as modifiers for process foods. However, nothing is known about their joint use with transglutaminase and an edible surface active agent, as a binding agent of raw food materials. As will be described in the following, such a joint use exerts markedly excellent effects.

It is generally known that, when a bound beef is prepared, binding of meat pieces to one another cannot be effected without the use of a binding agent. The inventors of the present invention have prepared a prototype bound beef sample, firstly preparing the enzyme preparation of the second embodiment of the present invention containing 1% by weight of sodium caseinate, 0.05% by weight of a sucrose fatty acid ester having an HLB value of 16 and transglutaminase in an amount of 1,000 units per 1 kg meat, dispersing and dissolving the thus prepared enzyme preparation in water in an amount of 3 times the weight of the preparation, mixing the resulting solution with round pieces and then allowing the resulting mixture to stand still for 30 minutes at room temperature. Tensile strength ($g/cm^2$) of the thus prepared prototype sample was measured using a rheometer manufactured by Fudo Kogyo Co., Ltd.

Tensile strength ($g/cm^2$) of the prototype sample was found to be 195, showing satisfactory binding and full fitness for the handling during processing without causing separation of meat pieces in the raw state. As described in the foregoing, binding of raw materials or cooking and processing performance of the bound product cannot be regarded as effective or acceptable when the tensile strength is less than 100 $g/cm^2$.

When 4 to 5 commercially available binding agents were used according to the respective prescriptions and the resulting bound products were evaluated in the same manner as described above, their tensile strengths were within an range of from 30 to 65 $g/cm^2$, with no values exceeding 100 $g/cm^2$. These results also support markedly excellence in the techniques of the present invention.

A third embodiment of the present invention relates to a process for the production of bound-formed foods which comprises adding an enzyme preparation of the first or second embodiment of the present invention to a raw food material and allowing said enzyme preparation to exert its function.

In this production process, the enzyme preparation of the present invention is used in such an amount that the binding effect is improved by the use of the inventive enzyme preparation in comparison with a case in which the enzyme preparation is not used.

From such a view point, the amount of the enzyme preparation of the present invention to be added to the raw food material consisting of one or more of animal meats, fishes and shellfishes, fish eggs, vegetables, fruits, process foods and the like is not particularly limited. Usually, it is used in an amount of from 5 to 20,000 units, preferably from 100 to 5,000 units, with respect to transglutaminase, in an amount of from 0.1 to 50 g, preferably 1 to 30 g, with respect to a casein, and in an amount of from 0.01 to 10 g, preferably from 0.1 to 5 g, with respect to an edible surface active agent, per 1 kg of such raw materials. It will be understood easily that those skilled in the art can easily prepare an enzyme preparation of the present invention by appropriately blending transglutaminase and casein or both of them and an edible surface active agent for the above ranges to be obtained.

In greater detail, an amount of transglutaminase added if smaller than 5 units per 1 kg of meat would bear no significant binding effect. On the other hand, its amount if larger than 20,000 units would cause reduction of binding capacity of, say a formed steak, thus resulting in a monotonous eating touch with rubbery resistance to the teeth.

An amount of casein added if smaller than 0.1 g per 1 kg of meat would bear no higher binding effect than the case of the single use of transglutaminase, while its amount if larger than 50 g would cause significant reduction of binding capacity in comparison with the case of the use of 50 g or smaller and also would cause development of casein-specific viscosity, taste and the like.

Furthermore an amount of an edible surface active agent added, if smaller than 0.01 g per 1 kg of meat, would bear no significant water dispersion improving effect on casein, while its amount if larger than 10 g would bear no proportionally greater effect but rather render the enzyme preparation uneconomical.

For the above reasons, it is preferable to use an enzyme preparation of the present invention within the aforementioned ranges with respect to the respective components. As a matter of course, these ranges are merely one standard and therefore are not binding.

Addition of the enzyme preparation of the present invention to a raw food material and subsequent effectuation of the enzyme reaction can be made with no particular difficulty, by simply mixing the enzyme preparation of the present invention with the raw food material and subsequently allowing the mixture to stand still under such conditions that the function of transglutaminase is effectuated. For example, the enzyme reaction may be carried out by allowing the mixture to stand still usually at a temperature of from 0° to 60° C., preferably from 5° to 40° C., for a period of from 5 minutes to 48 hours, preferably from 10 minutes to 24 hours. Such reaction conditions are general standards and therefore may be modified appropriately depending on the raw materials to be used and the like.

Incidentally, a little is to be added as follows. For sliced fresh carrot to be bound, an enzyme preparation of the present invention after preferably dissolved in water is applied onto the surface of two or more slices, whereby they are bound to each other at the applied surface as the binding interface. For boiled-sliced carrot to be bound, an enzyme preparation of the present invention is preferably applied as it is prepared, i.e., in the powder state, without being changed into its solution. With respect to sliced onion, an enzyme preparation of the present invention after preferably changed into its solution is applied to the surface of the slices. With respect to cooked beans, an enzyme preparation of the present invetion is preferably applied in the powder state, whereby two or more grains are bound to each other. With respect to sliced fruit, an enzyme preparation is preferably applied in the powder state. With respect to biscuit, cracker, chocolate, potato chip, cookie, pie and the like, an enzyme prerparation of the present invention is preferably applied as its solution onto the surface through which binding is to be effectuated.

Timing of the addition of the enzyme preparation of the present invention during the production process of a bound-formed food is not particularly limited, but it is preferable to add and mix the enzyme preparation just before the forming step in order to obtain the highest binding effect. With regard to the way of adding, the enzyme preparation may be applied to a raw food material directly or after dissolved in water, a seasoning liquid or the like.

From the viewpoint of the expression of binding capacity, it is preferable to add transglutaminase and a casein or transglutaminase, a casein and an edible surface active agent simultaneously, which is one of the important reasons why the two or three active components are used in the form of an enzyme preparation.

However, these active ingredients are not necessarily used after making into a form of an enzyme preparation. In consequence, a fourth embodiment of the present invention relates to a process for the production of bound-formed foods which comprises adding transglutaminase and a casein, or an edible surface active agent together with these two active agents, to a raw food material and allowing them to exert their functions.

When, for example, transglutaminase and a casein are separately purchased and used instead of using them in the form of an enzyme preparation of the present invention, it is preferable to construct the production process flow in such a way that both agents can be added as simultaneously as possible.

As a matter of course, transglutaminase and a casein are not necessarily added simultaneously. However, binding effect may be reduced slightly when they are not simultaneously added, because the transglutaminase reaction will be partial to either the meat protein in the raw food material or the casein. On the other hand, when transglutaminase and a casein are simultaneously added, sufficient binding effect is expressed because the casein can be functioned efficiently in the schema: meat protein-casein-meat protein.

The respective amounts of transglutaminase, a casein and an edible surface active agent, and the reaction conditions of transglutaminase according to this embodiment of the present invention can be the same as those described in relation to the bound-formed food production process of the third embodiment of the present invention. As a matter of course, various optional additives described in the foregoing in relation to the first embodiment of the present invention can be used appropriately in the production process of this embodiment of the present invention.

According to the present invention, sliced or small pieces of beef, pork, chicken, fish, squid, octopus and the like can be used singly or in a combination of two or more as the raw material. When an enzyme preparation of the present invention is used, or transglutaminase and a casein or transglutaminase, a casein and an edible surface active agent are used separately without making them into an enzyme preparation, timing of the addition of these agents is not particularly limited. In general, in the case of fish or meat jelly products produced from minced fish meat or ground animal meat as the main raw materials, as well as daily household dishes, these agents may be added directly to minced fish meat or ground animal meat when kneaded, independent of the time of kitchen salt addition.

Some of the bound-formed foods produced by the process of the present invention can be served at table directly. For example, binding-treated food materials such as fish eggs, shellfishes, vegetables, fruits and the like can be served at table as such more frequently than animal meats and the like.

In some cases, heating, freezing, refrigeration, retort treatment and the like treatments are required after the binding forming of the present invention (for example, retort humburg steak and frozen pork cutlet), and these treatments may be carried out if desired or necessary (for example, fries). As a matter of course, these heating, freezing and the like treatments may be employed in a combination of two or more thereof. That is, freezing treatment may be carried out after heating in one case, and freezing treatment may be carried out after retort treatment on the other case. For example, a raw food material may be formed into steak, pork cutlet, slice and the like shapes and then subjected to a retort treatment by packing the formed products in retort packings, or these formed foods may be coated and fried or boiled. Also, after these heating processing, the products may be frozen to be used as frozen food stuffs.

Finally, a method for the measurement of transglutaminase activity will be described. With respect to the present invention, the activity unit of transglutaminase is measured and defined as follows. That is, benzyloxycarbonyl-L-glutaminylglycine and hydroxylamine as substrates are allowed to react each other. The hydroxamic acid resulting from the reaction is converted into an iron complex in the presence of trichloroacetic acid, and then absorbance at 525 nm is measured to calculate the amount of hydroxamic acid using a calibration curve, thereby determining the activity (cf. Japanese Patent Application Laying-Open (Kokai) No. Hei 1-27471).

(Functions of the Invention)

According to the present invention, joint use of transglutaminase and a casein or joint use of these agents and an edible surface active agent as a third agent renders possible a novel means for the binding forming of raw food materials, which does not require an excess amount of kitchen salt that causes salty taste in the final products or generation of viscosity resulting from the salt dissociation of proteins, and which can be applied to the binding forming of one or a plurality of raw food materials selected from not only animal meats but also fishes, crustaceans, molluscs, shellfishes, fish eggs, vegetables, fruits, process foods and the like. Formed products thus produced can provide the same food qualities as those of common foods in terms of their appearances, eating touches, tastes and savors even when they are cooking-processed, retort-treated or frozen.

EXAMPLES

The following examples are provided to further illustrate the present invention. It is to be understood, however, that the examples are for purpose of illustration only and are not intended as a definition of the limits of the present invention.

Example 1

Four enzyme preparations of the present invention were prepared according to the recipes (a) to (d) shown in Table 1. As the transglutaminase, a transglutaminase (calcium-independent; specific activity, 1.0 unit/mg) produced by a microorganism belonging to the genus Streptoverticillium (*S. mobaraense* IFO 13819) was used.

TABLE 1

| Enzyme prep. No. | Enzyme preparations Recipe | |
|---|---|---|
| 1 | (a) sodium caseinate | 100 g |
|   | transglutaminase | 1,000 u |
| 2 | (b) sodium casein | 70 g |
|   | isolated soybean protein (ex Ajinomoto Co., Inc.) | 30 g |
|   | transglutaminase | 10,000 u |
| 3 | (c) sodium caseinate | 60 g |
|   | transglutaminase | 120,000 u |
|   | mannitol | 40 g |
| 4 | (d) milk powder | 100 g |
|   | transglutaminase | 1,000 u |

Each of the thus prepared enzyme preparations was added to, and mixed with, minced cod meat and the mixture was allowed to stand for about 1 hour at room temperature (25° C.) whereby it was converted into a minced cod product having an excellent binding capacity.

When each of these enzyme preparations were stored in the dark for one year at 25° C., decrease in specific activity was hardly observed. Also, when the enzyme preparations thus stored for one year were applied to minced cod meat in the same manner, each of the resulting minced products showed an excellent binding capacity.

Example 2

To 1,000 g of small pieces of ham (waste meat, about 2 cm cubic) were uniformly added, with mixing using a kneader, 10 g of sodium caseinate and (1) 0 unit, (2) 0.4 unit, (3) 1 unit, (4) 5 units, (5) 10 units or (6) 20 units, per 1 g of the waste meat, of the same transglutaminase used in Example 1 (calcium-independent; specific activity, 1.0 unit/mg; produced by *Streptoverticillium mobaraense* IFO 13819).

Thereafter, each of the mixtures thus prepared was packed into a casing tube having a folding width of 75 mm and allowed to stand for 1 hour at room temperature, whereby 6 raw bound meat samples having different enzyme levels were obtained.

Separately from this, each of 6 raw bound meat samples obtained in the same manner was packed into a casing tube, but stored for a whole day and night in a freezer at −25° C., and then thawed, whereby 6 frozen-thawed bound meat samples having different enzyme levels were obtained.

Each of the thus prepared 12 bound meat samples was removed from its casing and sliced into a thickness of about 9 mm using a kitchen knife, and the slices were subjected to the sensory evaluation by 10 skilled panelists to determine the binding capacities of the samples. The evaluation was carried out by a ten point method. That is, strong binding was given 10 points, certain binding but easy separation when pulled was given 5 points, and no binding was given 1 point.

The results are as follows. That is, binding scores in the case of the raw bound meats were 2.3 points for the first sample (control), 5.8 for the second, 9.1 for the third, 7.0 for the fourth, 5.6 for the fifth, and 4.1 for the sixth. In the case of the frozen-thawed bound meats, on the other hand, the binding scores were 2.9 points for the first sample (control), 6.0 for the second, 9.8 for the third, 7.8 for the fourth, 5.9 for the fifth and 3.9 for the sixth.

These results show that, in comparison with the control (no transglutaminase having been used), the binding effect by transglutaminase is increased when used jointly with a casein, and the effect is especially high when transglutaminase is used in an amount of from 0.4 to 10 units.

When the remaining slices were subjected to a grilling test, with respect to each case of the raw and frozen-thawed bound meat samples, the 2nd, 3rd, 4th and 5th samples showed no shrinkage after their grilling on a frying pan, having the same external appearance as a single large piece of meat was grilled.

When the above 6 raw bound meat samples were subjected to the tensile test using a rheometer manufactured by Fudo Kogyo Co., Ltd., their tensile strengths were found to be 25 g/cm$^2$ for the first sample, 120 g/cm$^2$ for the second, 191 g/cm$^2$ for the third, 127 g/cm$^2$ for the fourth, 105 g/cm$^2$ for the fifth, and 55 g/cm$^2$ for the sixed.

These results also show that, in comparison with the control, thr binding effect by transglutaminase is increased when used jointly with a casein, and the effect is especially high when transglutaminase is used in an amount of from 0.4 to 10 units.

Example 3

To 1,000 g of small pieces of chicken thigh (about 2 cm cubic) were added 5 g of sodium caseinate and 5 units per 1 g meat of the same transglutaminase used in Example 1, followed by mixing and subsequent 1 hour of standing in a refrigerator (5° C.), whereby a chilled bound chicken thigh sample (Sample 1).

A portion of the thus prepared bound meat sample was frozen for 1 week in a −25° C. freezer, and then thawed to obtain a frozen-thawed bound thigh sample (Sample 2).

When binding capacity scores for these samples were measured in the same manner as described in Example 1, both of Samples 1 and 2 showed an excellent binding capacity with a score of 8.2.

Example 4

An enzyme preparation for bound-formed food use of the present invention was prepared by mixing 5,000 units of the same transglutaminase used in Example 1 with 5 g of sodium caseinate.

The entire portion of the thus prepared enzyme preparation was mixed with 1,000 g of small pieces of chicken thigh (about 2 cm cubic). Thereafter, the mixture was allowed to stand for 1hour in a refrigerator (5° C.) whereby a chilled bound chicken thigh sample was obtained. When binding capacity score for the sample was measured in the same manner as described in Example 1, it showed an excellent binding capacity with a score of 8.3.

Though the results are almost the same as those of Example 3, the use of an enzyme preparation like the case of this example has an advantage in terms of simplicity.

When the thus obtained chilled bound thigh sample was cooked and subjected to an eating test, it showed excellent taste and eating touch.

Example 5

To 1,000 g of small pieces of beef flank (waste meat, about 5 cm cubic) were added 15 g of sodium caseinate and 1 unit per 1 g meat of the same transglutaminase used in Example 1, followed by 1 hour of standing in a refrigerator (5° C.), whereby a chilled bound beef sample (steak meat, Sample 1) was obtained. A portion of the thus prepared sample was frozen for a whole day and night in a −25° C. freezer, and then thawed to obtain a frozen thawed bound beef sample (Sample 2).

When binding capacity scores for these samples were measured in the same manner as described in Example 1, both of Samples 1 and 2 showed an excellent binding capacity with a score of 9 to 10. In addition, when both samples were grilled and subjected to an eating test, they showed a soft touch to the teeth and a juicy taste, thus indicating their high commercial values.

Example 6

An enzyme preparation for bound-formed food use of the present invention was prepared by mixing 1,000 units of the same transglutaminase used in Example 1 with 15 g of sodium caseinate.

The entire portion of the thus prepared enzyme preparation was mixed with 1,000 g of small pieces of beef flank (waste meat, about 5 cm cubic). Thereafter, the mixture was allowed to stand for 1 hour in a refrigerator (5° C.), whereby a chilled bound beef sample (steak meat) was obtained.

When binding capacity score for the sample was measured in the same manner as described in Example 1, it showed an excellent binding capacity with a score of 9 to 10. In addition, when the sample was grilled and subjected to an eating test, it showed a soft touch to the teeth, and a juicy taste, i.e., an excellent eating touch.

Example 7

To 1,000 g of hairy crab (*Erimacrus isenbeckii*) waste meat with the fibers loosened were added 3 g of milk powder and 3 unit per 1 g meat of the same transglutaminase used in Example 1. The mixture was wrapped with polyvinylidene chloride wrapping film for food wrapping use to form the mixture into the shape of crab arm meat, followed by overnight standing in a refrigerator (5° C.). The thus formed product had perfectly bound fibers and could be regarded as crab arm sinews.

A similar product was prepared as a control in the same manner except that transglutaminase was not used. The product showed an insufficient binding capacity.

Example 8

1,000 g of loose herring roe grains was uniformly mixed with 15 g of sodium caseinate using a kneader, and the transglutaminase described in Example 1 was uniformly added to the mixture in an amount of 10 units per 1 g roe, followed by 1 hour of standing at room temperature. The resulting mixture was put in a box tray (size; 10 cm×15 cm×3 ), and then allowed to stand for 16 hours in a refrigerator to obtain a formed herring roe sample.

When the thus obtained sample was sliced into a predetermined shape and used as a Japanese sushi matter, it showed the same eating touch as such herring roe as usually used as a sushi matter does.

A similar product was prepared as a control in the same manner except that transglutaminase was not used. The product was brittle and showed an inferior eating touch.

Example 9

1,000 g of sablefish (*Anoplopoma fimbria*) pieces (size; 3 cm×3 cm×2 cm) was uniformly sprinkled with 10 g of sodium caseinate dissolved in 5 ml of water, and arranged in a box tray (size; 20 cm×30 cm×5 cm). To this was sprayed 1.5 g of the transglutaminase described in Example 1 which had been suspended in 10 ml of water. In this instance, the amount of the used transglutaminase was about 1.5 units per 1 g sablefish meat. Thereafter, the resulting mixture was allowed to stand overnight in a refrigerator (5° C.).

The thus obtained sample was sliced into a thickness of about 20 mm, coated and then fried at a temperature of 170° to 180° C. to obtain a fried fish product. This product showed the same quality as a single fried fish slice of fish when fried does, and did not loosen.

Similar effects of the joint use of transglutaminase and a casein were observed when small pieces and waste meats of Spanish mackerel, tuna and the like were used.

Example 10

An enzyme preparation of the present invention was prepared by thoroughly mixing 1,500 units of transglutaminase with 9 g of sodium caseinate and 1 g of isolated soybean protein.

The thus obtained enzyme preparation was dissolved in 10 ml of water and, with sprinkling, uniformly added to 1,000 g of the same sablefish slices used in Example 9 which had been arranged in the same box tray used in Example 9. Thereafter, the resulting mixture was allowed to stand overnight in a refrigerator (5° C.).

The thus obtained sample was sliced into a thickness of about 20 mm, coated and then fried at a temperature of 170° to 180° C. to obtain a fried fish product. This product showed the same quality as a single fried fish slice and did not loosen. It also showed a markedly excellent taste and eating touch.

Example 11

470 g of beef-pork mixed ground meat was uniformly kneaded with 15 g of sodium caseinate and 1 unit per 1 g meat of the transglutaminase of as used in Example 1, and the mixture was further mixed with 6 g of kitchen salt, 4 g of sugar 4 g of sodium glutamate, 1 g of pepper, 1 g of ginger and 0.1 g of nutmeg. To the resulting mixture were further added 120 g of fresh egg white, 230 g of onion which had been cut into tiny pieces, 79 g of bread crumbs and 80 g of milk, followed by additional mixing, and formed the mixture into the shape of a hamburg steak.

The thus formed product was allowed to stand for 30 minutes at room temperature and then heated on a frying pan to obtain a hamburg steak product (Prototype sample A-1). As a control, another hamburg steak product (Prototype sample A-2) was prepared by repeating the same process for the production of Prototype sample A-1 except that sodium caseinate and transglutaminase were not used.

A portion of each of the thus prepared prototype samples was packed in a retort packing and retort-treated at $F_0$=6 to obtain retort products of Prototype samples A-1 and A-2 (Prototype samples B-1 and B-2).

Also, another portion of each of prototype samples A-1 and A-2 was stored in a freezer at −18° C. for a whole day and night to obtain frozen hamburg steak products (Prototype samples C-1 and C-2).

When these 6 prototype hamburg steak samples were evaluated by the organoleptic test, Prototype sample A-2 showed a homogeneous touch to the teeth with no feeling of meat granules, while Prototype sample A-1 showed excellent properties in terms of a hamburg steak-specific heterogeneous touch and a juicy feeling. As to the retort-treated products, Prototype sample B-2 showed a generally loose eating touch, while the qualities of Prototype sample B-1 were hardly changed by the retort-treatment retaining a touch of meat granules though its juicy feeling was slightly lower than that of Prototype sample A-1. With regard to the frozen products, Prototype sample C-2 showed a watery soft eating touch, while Prototype sample C-1 showed a meat-specific elasticity and juicy feeling with almost the same eating touch of its pre-freezing product.

Example 12

30 g of sodium caseinate and 1 unit per 1 g meat of the transglutaminase as described in Example 1 were added to 500 g of inside ham and 500 g of head pork and mixed for about 3 minutes using a food cutter. To the resulting mixture were further added 3.1 g of sodium glutamate, 3.5 g of beef extracts, 20 g of sugar, 2.9 g of pepper, 1 g of sage powder, 1 g of allspice powder and 150 g of ice water, followed by 1 to 2 minutes of additional mixing, whereby a Vienna sausage material was obtained.

The thus prepared material was packed into an edible artificial casing tube made of collagen having a folding width of 2.5 cm, dried at 55° C. for 15 minutes in a smoke chamber for the reaction of transglutaminase, followed by smoking treatment at 60° C. for 5 minutes, and then cooked at 80° C. for 30 minutes, whereby a Vienna sausage (Prototype sample A-1) was obtained.

As a control, another Vienna sausage (Prototype sample A-2) was prepared by repeating the above process for the production of Prototype sample A-1 except that sodium caseinate and transglutaminase were not used.

When these two prototype samples were evaluated by the sensory test, in comparison with Prototype sample A-2, Prototype sample A-1 showed an excellent binding capacity, a good crispness when cut off with the teeth and an excellent taste.

Example 13

An enzyme preparation for bound-formed food use of the present invention was prepared by mixing 1,000 units of the transglutaminase described in Example 1 with 25 g of sodium caseinate, 5 g of wheat gluten and 0.3 g of mannitol.

The whole portion of the thus prepared enzyme preparation was added to 500 g of inside ham and 500 g of head pork and mixed for about 3 minutes using a food cutter. To the resulting mixture were further added 3.1 g of sodium glutamate, 3.5 g of beef extracts, 20 g of sugar, 2.9 g of pepper, 1 g of sage powder, 1 g of allspice powder and 150 g of ice water, followed by 1 to 2 minutes of additional mixing, whereby a Vienna sausage material was obtained.

The thus prepared material was packed into the same edible artificial casing tube used in Example 12 and then subjected to drying for the reaction of transglutaminase, smoking and cooking in the same manner as described in Example 12, whereby a Vienna sausage (Prototype sample A-1) was obtained.

As a control, another Vienna sausage (Prototype sample A-2) was prepared by repeating the above process for the production of Prototype sample A-1 except that the enzyme preparation was not used.

When these two prototype samples were evaluated by the sensory test, in comparison with Prototype sample A-2, Prototype sample A-1 showed an excellent binding capacity, a good crispness when cut off with the teeth and an excellent taste.

Example 14

500 g of raw cuttlefish pieces (size; 10 mm×50 mm×5 mm) was uniformly mixed with 10 g of sodium caseinate using a kneader, followed by uniform addition of 0.5 g of the transglutaminase described in Example 1 and subsequent 1 hour of standing at room temperature. In this instance, the transglutaminase was used in an amount of about 0.5 unit per 1 g cuttlefish.

The thus prepared mixture was formed into a single layer sheet using a box tray having the same size as described in Example 9. The thus formed sheet was stored overnight in a freezer to obtain a formed cuttlefish sample. This sample had already been changed into a cuttlefish sheet even in its raw state, that is, immediately after its removal from the freezer.

This sheet, when cooked as it was or coated and fried, showed the same eating touch as that of usual raw cuttlefish.

Example 15

An enzyme preparation for bound-formed food use of the present invention was prepared by mixing 500 units of the transglutaminase described in Example 1 with 9 g of sodium caseinate and 1 g of starch.

The thus obtained enzyme preparation was uniformly mixed with 500 g of raw cuttlefish pieces having the same size as described in Example 14 using a kneader, followed by 1 hour of standing at room temperature. The thus prepared mixture was treated in the same manner as described in Example 14 to obtain a formed cuttlefish sample. Similar to the case of Example 14, this sample had already been changed into a cuttlefish sheet in its raw state, that is, immediately after its removal from the freezer.

This sheet, when cooked as it was and then subjected to the sensory evaluation, showed the same eating touch as that of usual raw cuttlefish.

Example 16

Frozen minced Alaska pollack was broken in its frozen state into flakes, and 1,000 g of the resulting flakes was mixed with 30 g of kitchen salt and 350 g of ice water using a silent cutter at 3,000 rpm for 5 minutes. To this were added 100 g of starch ("Ginrei" manufactured by Ajinomoto Co., Inc.), 15 g of egg white ("Egg White Powder", manufactured by Taiyo Kagaku Co., Ltd.), 40 g of Japanese mirin, 11 g of seasonings (3 g of "Chohmi Base KE" and 8 g of "Chohmi Base I-7" both manufactured by Ajinomoto Co., Inc.), 8 g of a crab flavor ("Crab Flavor CS" manufactured by Ogawa Koryo Co., Ltd. ) and 1.5 g of potassium sorbitanate, followed by mixing for 1 minute using a silent cutter at 3,000 rpm to obtain a kneaded material. The final kneaded material showed a temperature of about 8° C.

Then, the thus prepared material was passed through a sheet-forming nozzle having a clearance of 1.5 mm to form the material into a thin film sheet (thickness; about 1.5 mm). To the upper side of the thus formed sheet was spray-applied 90 g of an aqueous 8% sodium caseinate solution containing 10 units per 1 ml water of the transglutaminase described in Example 1.

The thus coated sheet was passed through a wire-cutting roller having an interval of 2 mm to cut the sheet into the form of noodles, and about 100 strings of the noodle-shaped product were bundled and cut with a knife into a length of about 10 mm. The resulting bundle was allowed to stand at 45° C. for 20 minutes and then heated for 15 minutes in a steamer to effect inactivation of the enzyme and sterilization, whereby a crab-flavored kamaboko (Prototype sample A) was obtained.

As a control, another crab-flavored kamaboko (Prototype sample B) was prepared by repeating the above process for the production of Prototype sample A except that an aqueous 8% sodium caseinate solution containing no transglutaminase was used.

When these two prototype samples were evaluated by the sensory test, Prototype sample B showed an insufficient completion and a kamaboko-like eating touch, while Prototype sample A which had been treated with transglutaminase showed a proper shape and a natural crab meat-like eating touch with proper touch to the teeth.

Example 17

2,000 g of inside ham blocks and 1,000 g of inside ham waste were mixed with 25% by weight of the pickle liquid shown in Table 2 to a total weight of 3,750 g.

TABLE 2

| Pickle liquid | |
|---|---|
| Raw material | Blending ratio (% by weight) |
| Soybean protein | 4 |
| Sodium caseinate | 4 |
| Kitchen salt | 3.2 |
| Phosphate | 1.2 |
| Lactose | 4 |
| Ascorbic acid | 0.2 |
| Sodium glutamate | 2 |
| Transglutaminase | 0.023 |
| City water | 81.4 |
| Total | 100 |

Then, the mixture was uniformly mixed with 30 g of sodium caseinate and then with 1 unit per 1 g meat of transglutaminase, and the resulting mixture was subjected to tumbling for 30 minutes at room temperature using a tumbler and then packed into an inedible casing tube made of polyvinylidene chloride and having a folding width of 125 mm, followed by degassing in a vacuum stuffer. The thus prepared sample was allowed to stand for 1 hour at room temperature, subjected to semi-freezing in a freezer at −40° C. to freeze its surface only, and then immediately sliced into a thickness of about 3 mm. The thus sliced sample was packed into a retort pouch, sealed and then subjected to retort treatment using a retort apparatus (123° C. 8 minutes, $F_0$ value of about 7), whereby a transglutaminase-treated roasted pork was prepared (Prototype sample A).

As a control, another roasted pork (Prototype sample B) was prepared by repeating the above process except that transglutaminase was not used in the pickle liquid and at the time of the tumbling.

When qualities of these two prototype samples were evaluated, Prototype sample A showed a similar touch to the teeth and taste to those of usual roasted pork, while Prototype B could hardly be regarded as a roasted pork, because it showed no juicy feeling but rather dry and crumbly eating touch and bad throat-passing feeling.

In addition, yields, after the retort treatment were about 80% in the case of Prototype sample A, but about 72% Prototype sample B, thus showing superior qualities of Prototype sample A and the effect of transglutaminase also from this point of view.

The additional examples of the present invention will be given in which a transglutaminase (specific activity, 1.0 unit/mg) produced by a microorganism belonging to the genus Streptoverticillium (*S. mobaraense* IFO 13819) is used unless otherwise noted.

Example 18

Six enzyme preparations of the present invention were prepared according to Recipes (a) to (f) shown in Table 3.

TABLE 3

Enzyme preparations

| Enzyme prep. No. | Recipe | |
|---|---|---|
| 1 | (a) transglutaminase | 1,000 u |
|   | sodium caseinate | 90 g |
|   | sucrose fatty acid ester (HLB = 16) | 10 g |
| 2 | (b) transglutaminase | 10,000 u |
|   | sodium caseinate | 90 g |
|   | sucrose fatty acid ester (HLB = 16) | 10 g |
| 3 | (c) transglutaminase | 100,000 u |
|   | sodium caseinate | 90 g |
|   | sucrose fatty acid ester (HLB = 16) | 10 g |
| 4 | (d) transglutaminase | 10,000 u |
|   | sodium caseinate | 95 g |
|   | sucrose fatty acid ester (HLB = 16) | 5 g |
| 5 | (e) transglutaminase | 10,000 u |
|   | sodium caseinate | 95 g |
|   | sucrose fatty acid ester (HLB = 10) | 5 g |
| 6 | (f) transglutaminase | 10,000 u |
|   | sodium caseinate | 50 g |
|   | sucrose fatty acid ester (HLB = 16) | 3 g |
|   | potato starch | 46 g |
|   | sodium chloride | 1 g |

Each of the thus prepared enzyme preparations was dispersed in water, and then added to and mixed with Alaska pollack small pieces or inside ham pieces, and the mixture was allowed to stand for about 1 hour at room temperature (25° C.) to obtain a bound meat product having an excellent binding capacity. Prior to the addition of these enzyme preparations, each of them was dispersed in water in an amount of 3 to 5 times their weight using a whisk, whereby each enzyme preparation was dispersed in an instant.

When each of these enzyme preparations were stored in the dark for one year at 25° C. decrease in specific activity was hardly observed. Also, when the enzyme preparations thus stored for one year were applied to Alaska pollack small pieces or inside ham pieces in the same manner, each of the bound meat products showed an excellent binding capacity.

Example 19

A total of 6 enzyme preparations were prepared by thoroughly mixing 10 g of sodium caseinate with 1 g of a sucrose fatty acid ester having an HLB value of 16 and (1) 0 unit, (2) 400 units, (3) 1,000 units, (4) 5,000 units, (5) 10,000 units or (6) 20,000 units of transglutaminase.

Each of the thus prepared enzyme preparations was dispersed and dissolved in water in an amount of 3 times their weight, and added to 1,000 g of small pieces of inside ham (waste meat, about 2 cm cubic), followed by uniform mixing. Thereafter, each of the mixtures thus prepared was packed into a casing tube having a folding width of 75 mm and allowed to stand for 1 hour at room temperature, whereby 6 raw bound meat samples having different enzyme levels were obtained.

Separately from this, each of 6 raw bound meat samples obtained in the same manner was packed into a casing tube, stored for a whole day and night in a freezer at −25° C. and then thawed to obtain 6 frozen-thawed bound meat samples having different enzyme levels.

Each of the thus prepared 12 bound meat samples was subjected to sensory evaluation in the same manner as described in Example 2. The results are as follows. That is, binding scores in the case of the raw bound meats were 1.8 points for the 1st sample, 6.8 for the 2nd, 9.3 for the 3rd, 7.4 for the 4th, 5.8 for the 5th and 5.0 for the 6th. In the case of the frozen-thawed bound meats, on the other hand, the binding scores were 2.0 points for the 1st sample, 7.0 for the 2nd, 9.8 for the 3rd, 7.9 for the 4th, 6.0 for the 5th and 5.2 for the 6th.

These results show that, in comparison with the control (no transglutaminase having been used), binding effect increases markedly when transglutaminase is used jointly with a casein and a surface active agent, and the effect is especially high when transglutaminase is used in an amount of from 400 to 10,000 units.

When the remaining slices were subjected to a grill test, raw and frozen-thawed bound meat samples (2), (3), (4) and (5) showed no shrinkage after their grilling on a frying pan, having the same external appearance as the case of grilling of a single piece of meat.

When the above 6 raw bound meat samples were subjected to a tensile test in the same manner as described in Example 2, their tensile strength was found to be 17 $g/cm^2$ for sample (1), 125 $g/cm^2$ for (2), 189 $g/cm^2$ for (3), 136 $g/cm^2$ for (4), 110 $g/cm^2$ for (5) and 58 $g/cm^2$ for (6).

These results also show that, in comparison with the control sample (1), binding effect increases markedly when transglutaminase is used jointly, and the effect is especially high when transglutaminase is used in an amount of from 400 to 10,000 units.

Example 20

An enzyme preparation was prepared by mixing 5 g of an enzymatic hydrolyzate of casein with 1 g of a sucrose fatty acid ester having an HLB value of 16 and 2,000 units of transglutaminase.

The thus prepared enzyme preparation was dispersed and dissolved in water in an amount of 3 times its weight and, with mixing, uniformly added to 1,000 g of small pieces of chicken thigh (about 2 cm cubic). Thereafter, the resulting mixture was packed into a casing tube having a folding width of 75 mm, and allowed to stand for 1 hour in a refrigerator (5° C.), whereby a chilled bound thigh prototype sample was obtained.

Another bound thigh prototype sample was prepared in the same way but frozen without removing the casing for 1 week in a −25° C. freezer, and then thawed to obtain a frozen-thawed bound chicken thigh prototype sample.

When binding capacity scores for these prototype samples were measured in the same manner as described in Example 19, both of the prototype samples showed an excellent binding capacity with a score of 8.5.

The two samples when cooked and eaten showed an excellent taste and eating touch.

Example 21

An enzyme preparation was prepared by mixing 15 g of sodium caseinate with 1 g of a sucrose fatty acid ester having an HLB value of 16, 0.1 g of sodium chloride and 1,000 units of transglutaminase.

The thus prepared enzyme preparation was dispersed and dissolved in water in an amount of 4 times its weight and uniformly mixed with 1,000 g of small pieces of beef flank (about 3 cm cubic). Thereafter, the mixture was allowed to stand for 1 hour at room temperature, whereby a chilled bound beef sample (for steak use, Sample 1). A portion of Sample 1 was frozen for a whole day and night in a −25° C. freezer and then thawed to obtain a frozen-thawed bound beef sample (Sample 2).

When binding capacity scores of these two sample were measured in the same manner as described in Example 19, they showed an excellent binding capacity with a score of 9 to 10.

In addition, when Samples 1 and 2 were grilled and subjected to an eating test, they showed a soft touch to the teeth and a juicy taste, thus indicating their high commercial values.

Example 22

An enzyme preparation was prepared by mixing 10 g of sodium caseinate with 1 g of a sucrose fatty acid ester having an HLB value of 16, 0.1 g of sodium chloride, 20 g of branched dextrin and 1,000 units of transglutaminase.

The thus prepared enzyme preparation was mixed uniformly with 1,000 g of small pieces of beef flank (about 3 cm cubic), and the mixture was packed into a forming box (size; 20 cm×30 cm×5 cm), allowed to stand for 1 hour at room temperature and then put in a freezer. The resulting frozen formed mixture was taken out of the freezer and then cut in its semi-frozen state into slices having a thickness of 2 to 3 mm. Thereafter, the thus prepared slices were directly put in boiling water as Japanese shabushabu beef, or roasted on an iron plate as roast beef, followed by an eating test. As the results, these slices showed no separation at the binding interface, and they showed an eating touch a similar to a single slice of beef.

As a control, a similar sample was prepared by repeating the same process except that transglutaminase was not used, but no binding was observed. The control sample was broken when sliced or put in boiled water.

In addition, various bound meat samples were prepared in the same manner by replacing the flank with other animal meats and fishes (chicken, pork, mutton, wild boar, duck, squid, cuttlefish, tuna and the like), as well as their parts (inside round, thigh, inside ham, shoulder, loin and the like), in such combinations as beef round-pork ham-chicken breast, chicken thigh-chicken breast, and the like. As the results, these samples showed no separation at the binding interface and they showed an eating touch similar to a single slice of meat.

Example 23

An enzyme preparation was prepared by mixing 10 g of sodium caseinate with 1 g of a sucrose fatty acid ester having an HLB value of 16, 0.1 g of sodium chloride and 1,000 units of transglutaminase.

The thus prepared enzyme preparation was dispersed and dissolved in water in an amount of 4 times its weight and mixed uniformly with 1,000 g of a beef-pork fillet 1:1 mixture, both fillets being in the form of small pieces of about 5 cm cubic, and the resulting mixture was allowed to stand for 1 hour at room temperature to obtain a beef-pork mixture bound meat prototype sample (for steak use, Sample 1). A portion of Sample 1 was frozen in a −25° C. freezer for a whole day and night and then thawed to obtain a frozen-thawed beef-pork mixture bound meat prototype sample (Sample 2).

When binding capacity scores of these two sample were measured in the same manner as described in Example 19, they showed an excellent binding capacity with a score of 9 or more. In addition, when these samples were grilled and subjected to an eating test, each of them showed a soft touch to the teeth and a juicy taste. Since beef and pork can be enjoyed at the same time in addition to these excellent qualities, these prototypes seem to have a high commercial value.

In addition, a beef-pork mixture bound meat sample having an excellent binding capacity was also obtained when the enzyme preparation was directly applied to the beef-pork fillet mixture without dispersing and dissolving the enzyme preparation in water.

Example 24

An enzyme preparation was prepared by mixing 5 g of sodium caseinate with 0.3 g of a sucrose fatty acid ester having an HLB value of 16, 0.1 g of sodium chloride, 10 g of branched dextrin and 3,000 units of transglutaminase.

The thus prepared enzyme preparation was dispersed and dissolved in water in an amount of 4 times its weight and mixed uniformly with 1,000 g of hairy crab waste meat with its fibers, loosened, and the resulting mixture was wrapped with a wrapping film for food use to form the mixture into the shape of crab arm meat, followed by overnight standing in a refrigerator (5° C.). The thus formed product had perfectly bound fibers and could be regarded as crab arm sinews. In addition, this product showed a better binding capacity than the product obtained in Example 7.

A similar product was prepared as a control in the same manner except that transglutaminase was not used, but the product showed no binding.

Example 25

An enzyme preparation was prepared by mixing 15 g of sodium caseinate with 0.5 g of a sucrose fatty acid ester having an HLB value of 16, 0.1 g of sodium chloride, 4 g of potato starch and 5,000 units of transglutaminase.

The thus prepared enzyme preparation was dispersed and dissolved in water in an amount of 3 times its weight and mixed uniformly with 1,000 g of loose herring roe grains, and the resulting mixture was put in the same box tray as used in Example 8, followed by 1 hour's standing at room temperature and subsequent storage in a refrigerator to obtain a formed herring roe sample.

When the thus obtained sample was sliced into a predetermined shape and used as a Japanese sushi matter, it showed the same eating touch of herring roe usually used as a Japanese sushi matter. In addition, this sample when compared with the sample obtained in Example 8, was slightly worse in binding capacity, but could be eaten as food without any problem.

A similar product was prepared as a control in the same manner except that transglutaminase was not used, but the product was brittle and showed an inferior eating touch.

Example 26

An enzyme preparation was prepared by mixing 10 g of sodium caseinate with 0.2 g of a sucrose fatty acid ester having an HLB value of 16, 0.1 g of sodium chloride and 1,500 units of transglutaminase.

The thus prepared enzyme preparation was dispersed and dissolved in water in an amount of 3 times its weight and mixed uniformly with 1,000 g of sablefish slices having the same size as described in Example 9, and the mixture was arranged in a box tray having the same size as described in Example 9 and then allowed to stand overnight in a refrigerator (5° C.).

The thus obtained sample was sliced into a thickness of 15 mm, coated and then fried at a temperature of 170° to 180° C. to obtain a fried fish product. This product showed the same quality as a single fried fish slice and did not loosen.

The enzyme preparation used in this example also showed the same effects when applied to slices and waste meats of Spanish mackerel, tuna and the like.

Example 27

An enzyme preparation was prepared by mixing 15 g of sodium caseinate with 0.5 g of a sucrose fatty acid ester having an HLB value of 16, 0.1 g of sodium chloride and 1,500 units of transglutaminase.

The thus prepared enzyme preparation was dispersed and dissolved in water in an amount of 3 times its weight and then mixed uniformly with 1,000 g of scallop adductor muscle, and the mixture was formed by arranging it in a box tray having the same size as described in Example 26, allowed to stand for 1 hour at room temperature and then put in a freezer to obtain a bound-formed scallop meat sample.

When the thus obtained sample was cut into slices having a predetermined shape, put in boiling water as a scallop meat product for the Japanese shabushabu use and then subjected to an eating test, these slices showed an excellent eating touch without causing separation.

As a control, a similar sample was prepared by repeating the same process except that transglutaminase was not used, but no binding was observed and the control sample was broken when sliced or put in boiled water.

In addition, when the above enzyme preparation was directly applied to scallop adductor muscle without dissolving it in water, a scallop meat product for the shabushabu use having an equally excellent binding capacity was obtained.

Example 28

An enzyme preparation was prepared by mixing 10 g of sodium caseinate with 0.2 g of a sucrose fatty acid ester having an HLB value of 16, 0.1 g of sodium chloride and 1,000 units of transglutaminase.

The thus prepared enzyme preparation was dispersed and dissolved in water in an amount of B times its weight and mixed uniformly with 500 g of beef round and 500 g of Spanish mackerel white meat, and the resulting mixture was formed by piling them up in a box tray having the same size as described in Example 26, allowed to stand for 1 hour at room temperature and then put in a freezer to make the formed product into a semi-frozen state, which was subsequently cut into slices having a thickness of 1 to 2 cm.

When the slice was grilled on an iron plate as a beef and fish steak, separation at the binding interface did not occur and the grilled steak showed almost the same touch to the teeth as a single meat slice.

Also, when the semi-frozen product was sliced into a thickness of 2 to 3 mm as a meat product for the Japanese shabushabu use and heated for 6 to 7 seconds in a boiling soup, separation at the binding interface did not occur and the boiled slice showed almost the same touch to the teeth as a single meat slice similar to the above case.

Example 29

An enzyme preparation was prepared by mixing 10 g of sodium caseinate with 3.0 g of a sucrose fatty acid ester having an HLB value of 16, 0.5 g of sodium chloride and 12,000 units of transglutaminase. The thus prepared enzyme preparation was dispersed and dissolved in water in an amount of 4 times its weight to obtain an aqueous enzyme preparation solution.

Using a spatula, the thus obtained aqueous enzyme preparation solution was coated on the surface of 300 g of sliced cheese, 200 g of sliced cucumber and 500 g of sliced loin ham, and these coated slices were formed by piling them up in a box tray (size; 20 cm×30 cm×5 cm), followed by 1 hour's standing at room temperature, and held in a refrigerator. Thereafter, the thus formed sample was cut into slices having a predetermined shape to obtain a food product for hots d'oeuvre use made of cheese, cucumber and ham.

This product did not loosen and showed an excellent taste and appearance. Thus, it is evident that binding of various foods can be effected by the use of an enzyme preparation of the present invention.

As a control, a similar sample was prepared by repeating the same process except that transglutaminase was not used, but no binding was observed and the control sample was broken when sliced.

Example 30

5 g of sodium caseinate, 1 g of a sucrose fatty acid ester having an HLB value of 16, 0.1 g of sodium chloride and 2,000 units of transglutaminase were separately dispersed and dissolved in water in an amount of 3 times their weight, and each resulting solution was mixed uniformly with 1,000 g of chicken small pieces of thigh (about 2 cm cubic).

Thereafter, the resulting mixture was packed into a casing tube having a folding width of 75 mm and then allowed to stand for 1 hour in a refrigerator (5° C.), whereby a chilled bound thigh prototype sample was obtained, which showed an excellent binding capacity.

When the thus obtained chilled bound thigh was cooked, it showed an excellent taste and eating touch.

Thus, it is evident that the binding effect can be obtained not only by the use of the essential components in the form of an enzyme preparation but also by their separate use though a little complex in handling.

(Effects of the Invention)

According to the present invention, (1) waste meats resulting, e.g., from slaughter of beef cattle, pigs, chickens, fishes and the like and from the process steps of bird and animal meats and marine products can be bound strongly, thus rendering possible production of novel bound-formed foods making use of natural resources efficiently, and (2) one or a plurality of foods such as animal meats, fishery products, vegetables, fruits, process foods and the like can be bound strongly, thus rendering possible easy production of for example an unnaturally large beef fillet steak by binding beef fillets one another or new bound-formed foods having novel functions by binding different types of foods one another.

The bound-formed foods thus produced are highly practicable because they have an excellent eating touch and taste, as well as superior cooking, processing and the like abilities.

In addition, the use of an enzyme preparation of the present invention has an advantage in that a bound-formed food of interest can be obtained easily and simply, because it is not necessary to weigh transglutaminase, caseins, edible surface active agents and the like separately at the production site of the food of interest.

What is claimed is:

1. An enzyme preparation for binding of raw food materials, comprising:

20–99% by weight of a protein selected from the group consisting of casein, calcium caseinate, potassium caseinate, sodium caseinate, casein-containing milk powder and mixtures thereof;

0.01–15% by weight of an edible surface active agent selected from the group consisting of a sucrose fatty acid ester and a sorbitan fatty acid ester; and 1–50,000 units of transglutaminase per gram of said protein in said preparation.

2. The enzyme preparation according to claim 1, wherein said preparation further comprises at least one ingredient selected from the group consisting of an edible filler and an electrolyte.

3. The preparation according to claim 1, wherein said transglutaminase is present in an amount of from 10 to 5,000 units per gram of said protein in said preparation.

4. The enzyme preparation according to claim 1, wherein said protein is present in an amount of from 70–90% by weight.

5. The enzyme preparation according to claim 1, wherein said transglutaminase is calcium-independent.

6. The enzyme preparation according to claim 1, wherein said transglutaminase is calcium-dependent.

* * * * *

UNITED STATES PATENT AND TRADEMARK OFFICE
CERTIFICATE OF CORRECTION

PATENT NO. : 5,518,742　　　　　　　　　　　　　　Page 1 of 2
DATED　　　 : May 21, 1996
INVENTOR(S) : Soeda et al.

It is certified that error appears in the above-identified patent and that said Letters Patent is hereby corrected as shown below:

Column 2, line 64, "an binding", should read

--a binding--.

Column 3, line 16, "glutamine amino", should read

--glutamine amido--.

Column 9, line 49, "present invetion", should read

--present invention--.

Column 12, line 67, "the sixed", should read

--the sixth--.

Column 13, line 2, "thr", should read

--the--.

Column 15, line 26, "4g of sugar 4g of sodium", should read

--4g of sugar, 4g of sodium--.

UNITED STATES PATENT AND TRADEMARK OFFICE
CERTIFICATE OF CORRECTION

PATENT NO. : 5,518,742
DATED : May 21, 1996
INVENTOR(S) : Soeda et al.

It is certified that error appears in the above-identified patent and that said Letters Patent is hereby corrected as shown below:

Column 21, line 32, "touch a similar", should read

--touch as similar--.

Column 24, line 21, "hots d'oeuvre", should read --hors d'oeuvre--.

Signed and Sealed this

First Day of April, 1997

BRUCE LEHMAN

Attest:

Attesting Officer

Commissioner of Patents and Trademarks